United States Patent [19]

Piva

[11] Patent Number: 5,545,869
[45] Date of Patent: Aug. 13, 1996

[54] ELECTRICAL APPARATUS FOR DESTROYING SURGICAL INSTRUMENTS

[76] Inventor: Maria T. Piva, 1, Avenue Henry Dunant, Montecarlo, Monaco

[21] Appl. No.: 356,404

[22] PCT Filed: Jun. 28, 1993

[86] PCT No.: PCT/EP93/01649

§ 371 Date: Dec. 28, 1994

§ 102(e) Date: Dec. 28, 1994

[87] PCT Pub. No.: WO94/01153

PCT Pub. Date: Jan. 20, 1994

[30] Foreign Application Priority Data

Jul. 1, 1992 [IT] Italy .................. MI92A1604

[51] Int. Cl.$^6$ ............................................. B23K 11/22
[52] U.S. Cl. ........................................................... 219/68
[58] Field of Search .................................................. 219/68

[56] References Cited

U.S. PATENT DOCUMENTS

| | | | |
|---|---|---|---|
| 4,877,934 | 10/1989 | Spinello | 219/68 |
| 4,961,541 | 10/1990 | Hashimoto | 219/68 |
| 5,076,178 | 12/1991 | Kohl et al. | 219/68 |
| 5,138,125 | 8/1992 | Salesses | 219/68 |
| 5,212,362 | 5/1993 | Burden et al. | 219/68 |
| 5,264,675 | 11/1993 | Butler | 219/68 |
| 5,288,964 | 2/1994 | Walker et al. | 219/68 |
| 5,300,752 | 4/1994 | Elmerick et al. | 219/68 |

FOREIGN PATENT DOCUMENTS

| | | |
|---|---|---|
| 332584 | 9/1989 | European Pat. Off. . |
| 517643 | 9/1992 | European Pat. Off. . |
| 2211420 | 7/1989 | United Kingdom . |

*Primary Examiner*—Geoffrey S. Evans
*Attorney, Agent, or Firm*—Welsh & Katz, Ltd.

[57] ABSTRACT

Apparatus for destroying surgical instruments including a containment body having an insertion plate for receiving the instruments and a panel made of an electrically conducting material, in which the plate and panel are respectively electrically connected to a first pole and a second pole of an electric current generator. The plate is arranged on a traction and removal unit for receiving and removing the instruments from a holding element, and for pushing the instruments against the panel such as to provoke a melting current discharge through the instruments. An insertion sensor is also provided for activating the traction and removal unit upon insertion of the instruments in the insertion plate.

9 Claims, 5 Drawing Sheets

ELECTRICAL APPARATUS FOR DESTROYING SURGICAL INSTRUMENTS

TECHNICAL FIELD

The present invention relates to an apparatus for destroying surgical instruments, particularly hypodermic needles and scalpels.

BACKGROUND ART

As is known, especially in the health- and beauty-care sectors, there is the problem of neutralizing and eliminating disposable surgical medical instruments such as blades, scalpels, needles, pointed instruments and the like which are normally used in medical, dental or beauty-care treatments or for epidermal use and which, during their use, have been in contact with the patient's blood. In order to avoid risks of contagion or cross-contamination, for medical and paramedical personnel and for anyone who may come into contact with the used instruments, it is necessary to neutralize and destroy these instruments.

Devices which melt metallic surgical instruments by means of the flow of electric current of appropriate intensity have already been marketed for performing this operation.

Known from U.S. Pat. No. 5,076,178 is an apparatus for destroying syringe needles comprising a housing having an orifice for the insertion of needles, crimping means for crimping syringe needles to substantially seal the syringe and means for establishing an electric current through the needles.

However, U.S. Pat. No. 5,076,178 shows an apparatus having an orifice for the insertion of only needles and moreover it is necessary to carry out some manual operations in order to ensure the performance of the method of destruction. Therefore the apparatus is not useful for destroying scalpels and moreover, requires that an operator performs the operations manually until the needles are destroyed.

Also known from GB-A-2 211 420 is an electric needle destroyer, which is able to destroy needles by means of the flow of electric current. Even the apparatus herein described requires manual interventions until the needles are completely destroyed.

In known devices, in practice, it is necessary to insert the instrument to be destroyed into the device while continuing to apply a slight pressure until the instrument is completely destroyed.

This operation is a source of considerable dangers, since it not possible to assuredly prevent accidental contact with the instrument during the destruction operation, producing lesions with the possibility of contagion; furthermore, the instrument to be destroyed may inadvertently be removed from the device before it is completely destroyed, thus eliminating certainty in the neutralization of the potential dangers deriving from the instrument.

This is one of the most negative aspects of known devices, since the instrument to be destroyed, for example a needle, can be removed at the operator's discretion in any moment of the cycle, with a consequent difference in the length of the residual needle stump, which can still represent a considerable danger.

DISCLOSURE OF THE INVENTION

An aim of the present invention is indeed to eliminate the drawbacks described above by providing an apparatus for destroying surgical instruments, particularly hypodermic needles and scalpels, which allows to perform, with an automatic sequence, all the operations for destroying the instrument without requiring the operator to hold the instrument after inserting it into the apparatus.

Within the scope of the above aim, a particular object of the present invention is to provide an apparatus which allows to destroy not only hypodermic needles, as occurs with known devices, but also scalpel blades and other metallic objects.

Another object of the present invention is to provide an apparatus in which, for example in the case of needles, the remaining stump has a metallic portion which, besides being extremely short, is also completely closed, thus avoiding the possibility of outward leakage of any medical products, which may always represent a potential danger.

Another object of the present invention is to provide an apparatus for destroying surgical instruments which, by virtue of its particular constructive characteristics, is capable of giving the greatest assurances of reliability and safety in use.

This aim, these objects and others which will become apparent hereinafter are achieved by an apparatus for destroying surgical instruments, particularly for hypodermic needles and scalpels, as defined in the appended claims.

BRIEF DESCRIPTION OF THE DRAWINGS

Further characteristics and advantages of the present invention will become apparent from the description of a preferred but not exclusive embodiment of an apparatus for destroying surgical instruments particularly for hypodermic needles and scalpels, according to the invention, illustrated only by way of non-limitative example in the accompanying drawings, wherein.

WAYS OF CARRYING OUT THE INVENTION

Figure 1:
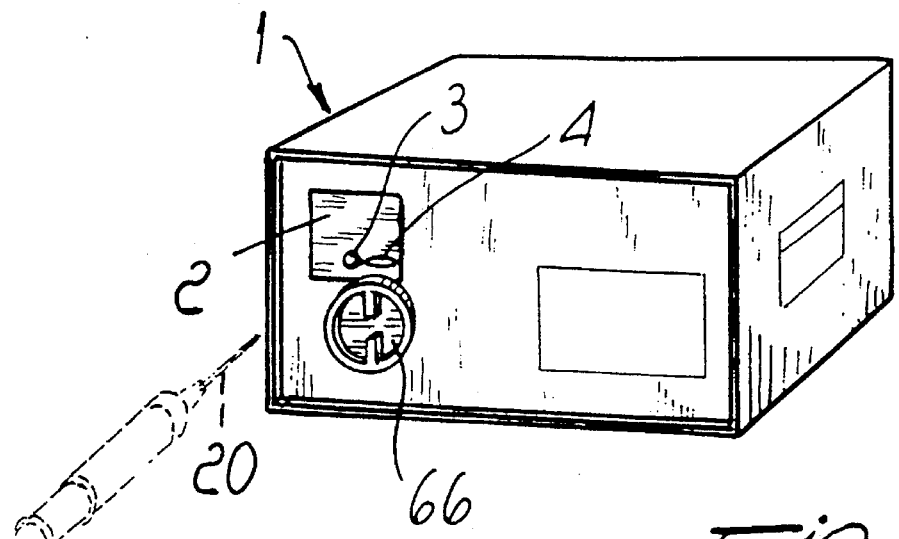
FIG. 1 is a schematic view of the apparatus according to the present invention.
Figure 2:
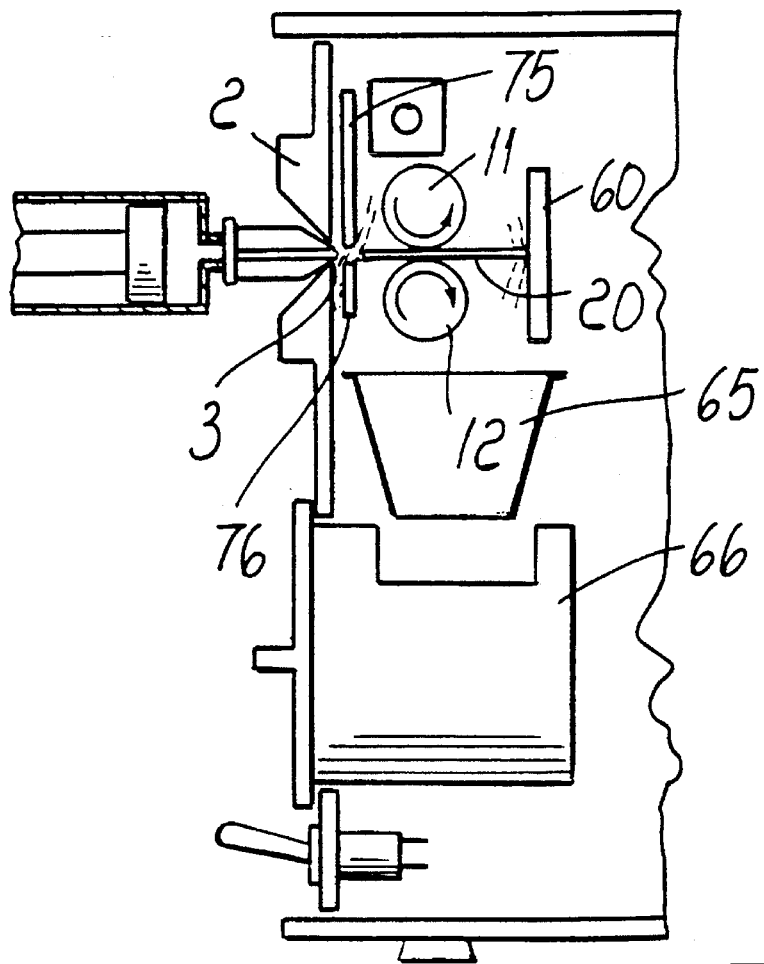
FIG. 2 is a schematic view of the operation of the apparatus.
Figure 3:
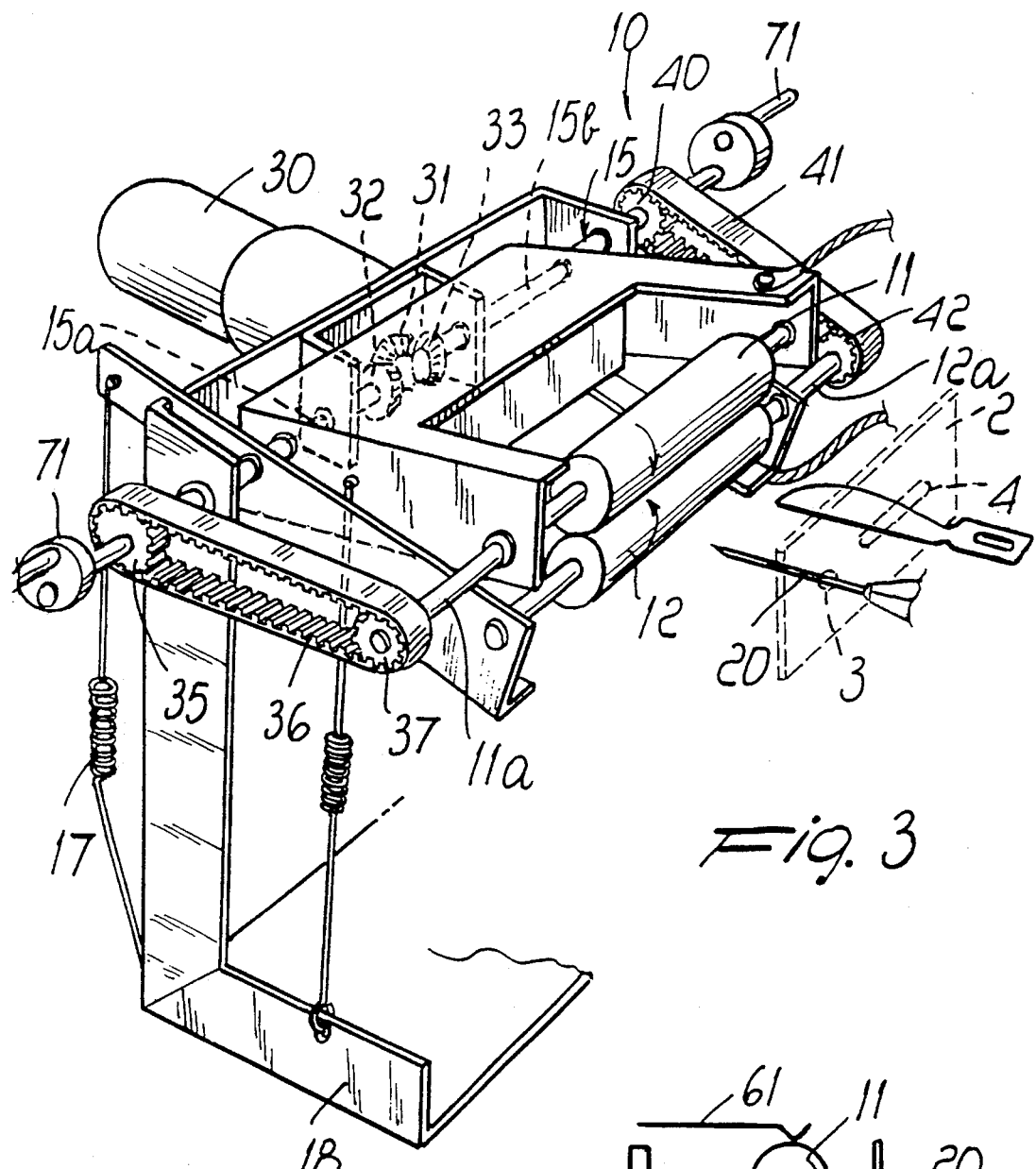
FIG. 3 is a perspective view of the removal and traction unit.
Figure 4:
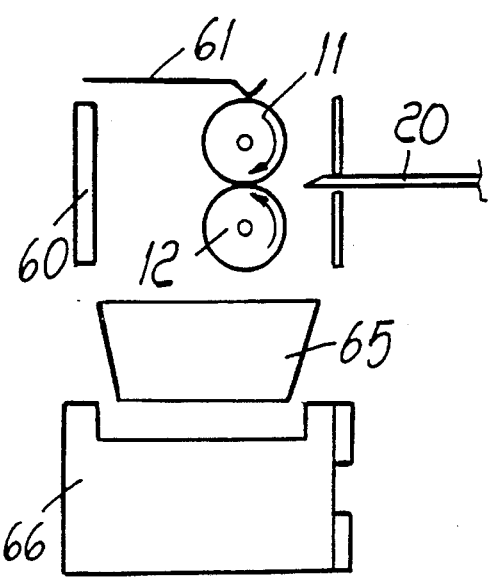
FIG. 4 is a schematic view of the step of the removal of a needle.

With reference to the above figures, the apparatus for destroying surgical instruments, particularly hypodermic needles and scalpels, according to the present invention, comprises a box-like or containment body, generally designated by the reference numeral 1, which forms, for example on its front face, a plate 2 for the insertion of the surgical instruments, which may be needles, scalpels, blades and any other metallic object; the plate 2 is removable in order to allow periodic cleaning and disinfection.

A hole 3 for the insertion of needles and a slot 4 for the insertion of scalpels and the like are formed on the plate 2.

Said insertion plate is arranged at a unit for the removal and traction of the instruments to be destroyed, generally designated by the reference numeral 10 and is provided with a first roller 11 and a second roller 12 which rotate in mutually opposite directions and are supported respectively by a first frame 13 and by a second frame 14; said frames are mutually pivoted at an axis 15, so as to provide a clamp-like coupling which keeps the rollers 11 and 12 in mutual contact although it allows mutual spacing according to the thickness of the instrument to be destroyed which is interposed between them. The unit for removal and traction of the instruments to be destroyed may be substituted by other mechanical means having the same function, such as pincers or the like.

In order to keep the rollers 11, 12 in mutual contact, elastic closure means are provided, constituted by a first spring 16, which is connected between the fixed structure 18 of the framework and the first frame, and by a second spring 17, which also acts between the fixed structure and the second frame.

The connection of the elastic means is such that it applies a force which tends to close the rollers together.

In order to rotationally actuate the rollers, which turn in mutually opposite directions so as to pull or entrain the instrument to be destroyed, which is designated by the reference numeral 20 both in the case of a needle and in the case of a blade, there are motor means 30 which mesh, by means of an associated reduction unit and a bevel gear 31, with bevel pinions 32 and 33 respectively keyed on the half-shafts 15a and 15b, which are arranged along the same line and also constitute the oscillation axis of the frames 13 and 14.

Kinematically, there is a first gear 35 keyed on the shaft 15a; a first belt 36 winds around said gear 35 and meshes with a first toothed pinion 37 keyed on the first shaft 11a for supporting the roller 12; in a similar manner, a second toothed gear 40 is keyed on the half-shaft 11b, and a second toothed belt 41 meshes with said gear 40 and winds around a second toothed pinion 42 keyed on the shaft 12a for supporting the roller 12.

With this arrangement, the rollers 11 and 12 assume mutually opposite rotation directions.

It is naturally possible to use other kinematic systems which allow to obtain the same function.

The apparatus furthermore comprises an insertion sensor which activates the motor 30 when the instrument 20 is inserted by means of the insertion plate.

Figure 5:
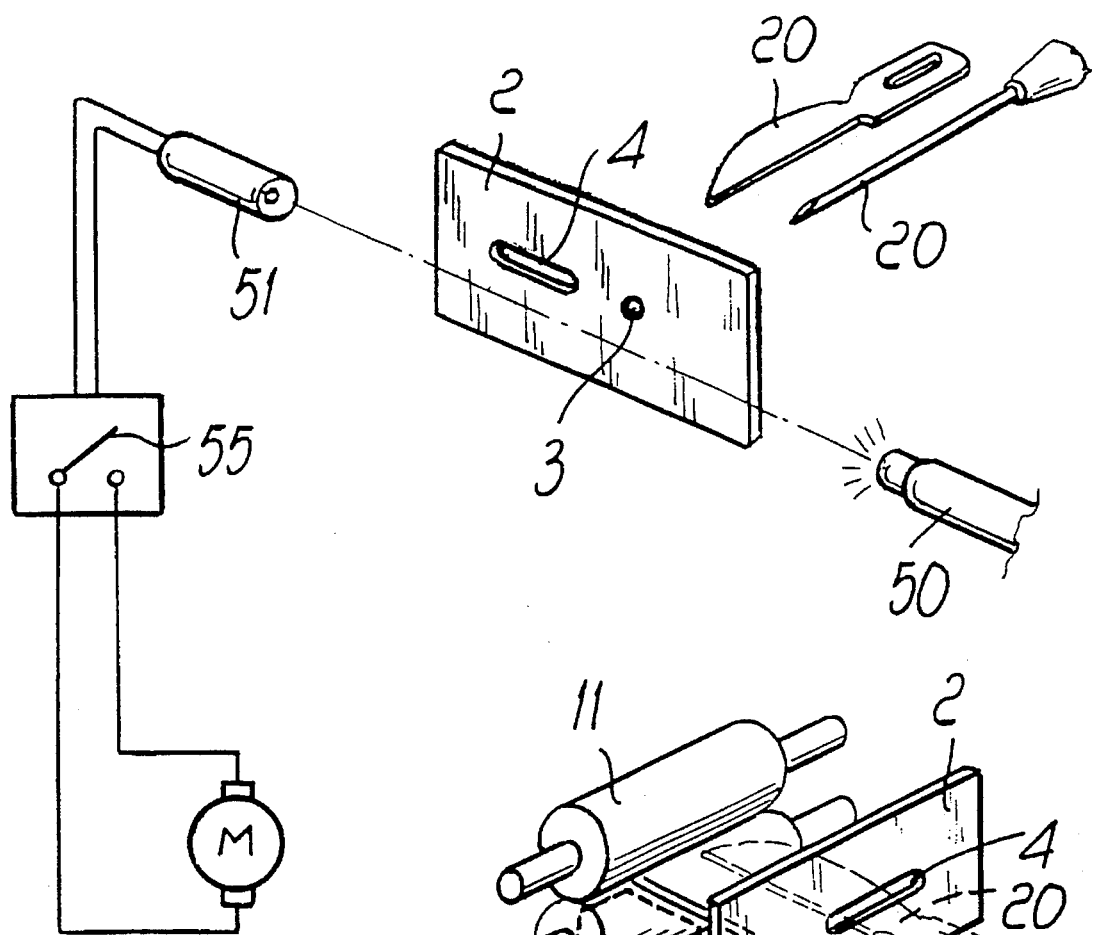
FIG. 5 is a view of an insertion sensor of the photocell type.
Figure 6:
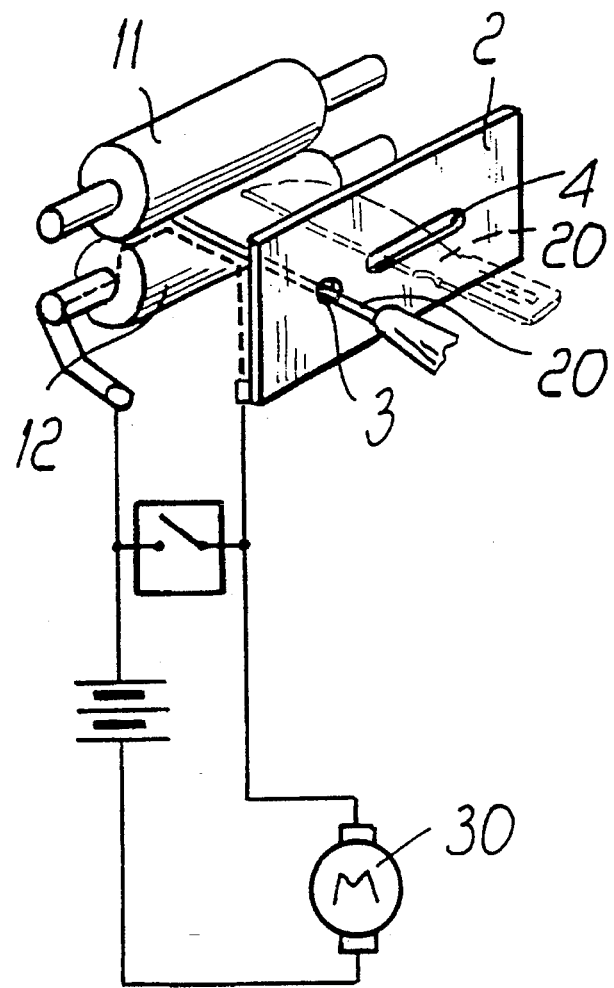
FIG. 6 is a view of an electrically activated insertion sensor.
Figure 7:
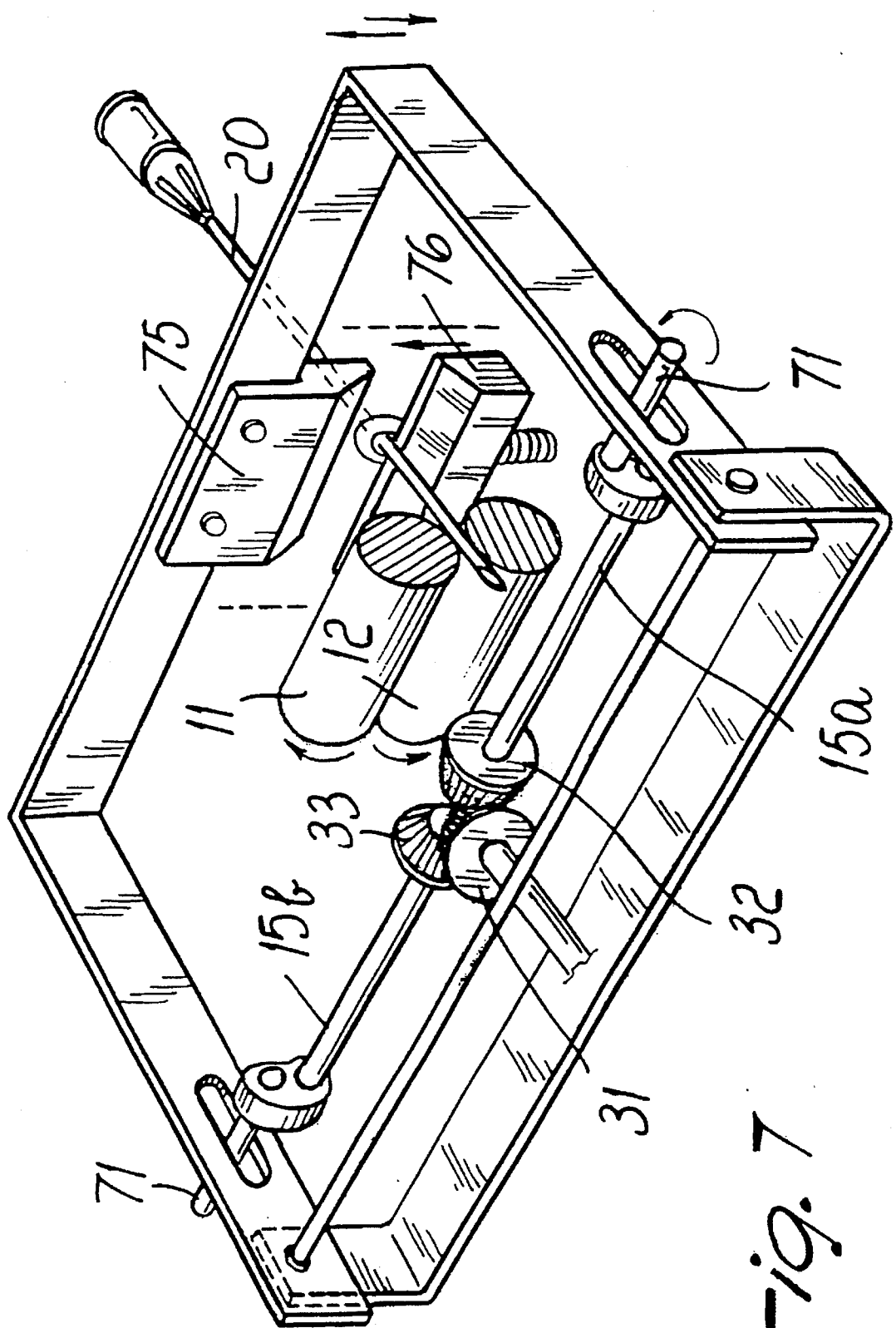
FIG. 7 is a schematic perspective view of the unit for cutting the inserted instrument.
Figure 8:
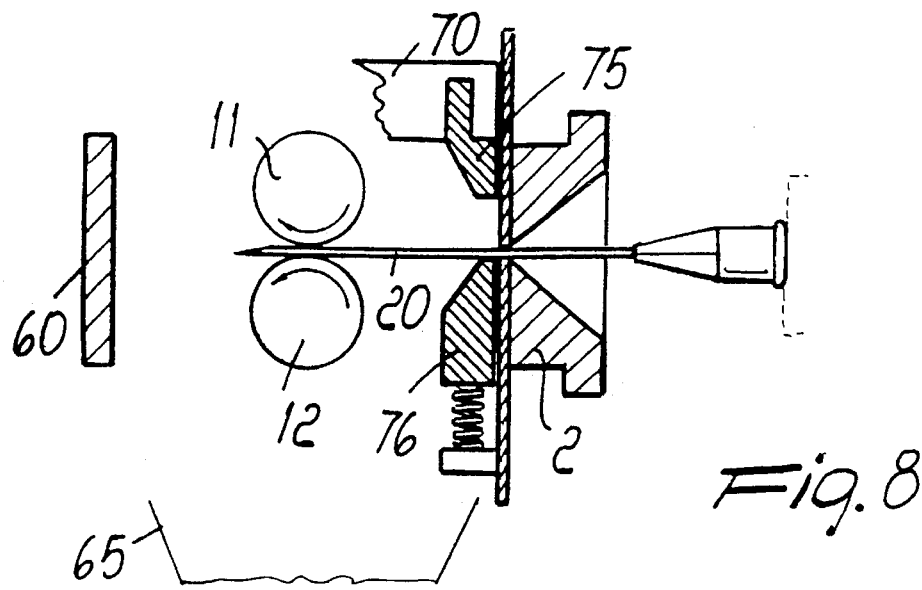
FIG. 8 is a sectional view of the initial step of the insertion of a needle, with the cutting means in a deactivated position.
Figure 9:
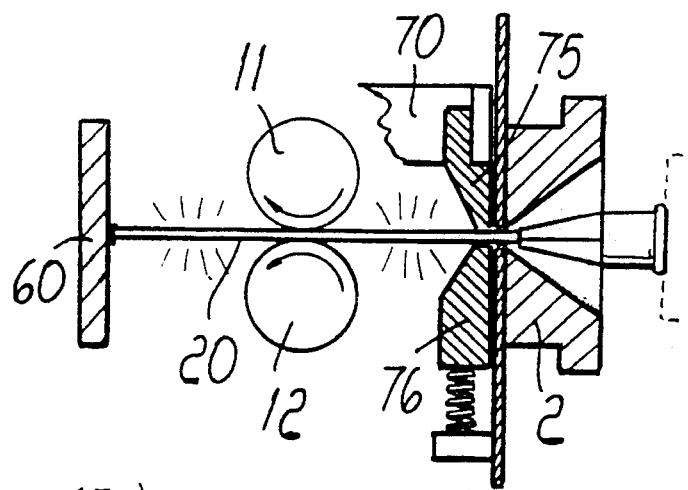
FIG. 9 is a view of the step of the activation of the cutting means.
Figure 10:
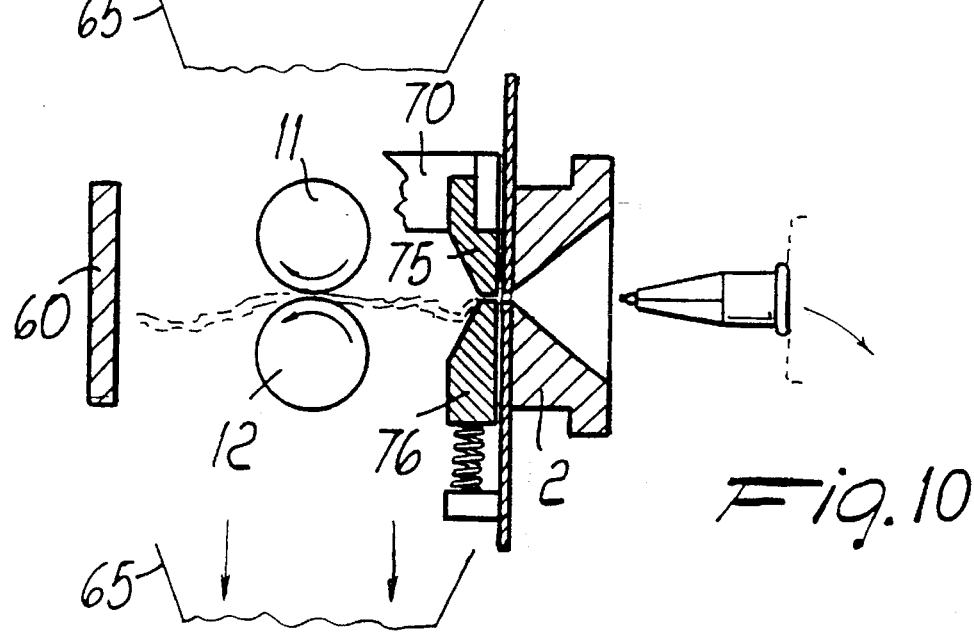
FIG. 10 is a view of the final step of the destruction of the needle.

Said insertion sensor, as shown in FIG. 5, can be constituted by an optical emitter 50 which emits a beam arranged at the insertion region 3 and 4 of the insertion plate 2; this beam is received by the receiving photocell 51, which, when the beam is interrupted due to the insertion of an instrument 20, closes the activation contact 55 for actuating the motor 30.

According to another embodiment, the activation sensor may be of the electrical type, exploiting the fact that when the needle is inserted, an electrical circuit on the plate 2 is closed; in this case, said plate is connected to one polarity and one of the rollers 11 or 12 is connected to the other polarity, so that there is a flow of current which actuates a toggle contact 57, which in turn actuates the motor 30 provided with a conventional reduction unit.

In order to melt the needle downstream of the removal and traction unit, there is a panel 60 made of electrically conducting material which is connected to a pole of a generator, which can be constituted by a transformer or possibly by a battery; the rollers 11 and 12 are instead connected to the other pole of the same generator, for example by means of a sliding contact 61, thus closing the electric circuit through the instrument 20, which is melted at high temperature, thus causing the complete destruction of the needle; the related waste falls, by means of a hopper 65, into a container 66 which is advantageously of the safety type, i.e. is closed when it is removed from the apparatus to take it away.

The apparatus furthermore comprises a cutting unit which allows to minimize the needle stump connected to the plastic cone and furthermore seals said stump tight.

Said cutting unit, as more clearly shown in FIGS. 7 to 10, has a cutting frame 70 which is oscillatably mounted and actuated by eccentric elements 71 keyed on the half-shafts 15a and 15b.

The frame supports, in a front region, a striker block 75 arranged above an anvil 76 arranged inside the body at the insertion plate 2, so that the striker moves substantially flush to said plate.

The striker is electrically connected to the same electrical connection pole as the panel, so that when the striker makes contact with the instrument 20, for example constituted by a needle, current flows inside the needle and melts it, and its stump is compressed due to the shears-like coupling between the striker 75 and the anvil 76.

In this manner, cutting by melting is performed on the needle stump, furthermore obtaining a compression which seals the needle tightly.

In practical operation, the apparatus according to the present invention allows to automatically destroy disposable surgical instruments, such as for example needles, scalpel blades and the like; it is in fact sufficient for the user to insert the instrument 20, by means of the insertion plate 2, by simply moving it into contact with the rollers, which are actuated automatically by the insertion of the instrument 20.

At this point the operator can release the instrument to be destroyed, since the rollers automatically grip it and pull it until it comes into contact with the panel, thus closing the contact and starting the melting of the needle.

The cycle generated by the coupling of the eccentric elements 71 produces, after a preset period, the activation of the cutting unit, with the descent of the striker 75 onto the anvil 76 and the consequent cutting of the needle stump by melting and compression.

In this manner, any possible danger of contact by the operator is eliminated and maximum safety is ensured.

Furthermore, the mounting of the rollers so that they can oscillate allows to easily adapt to all needle thicknesses and allows to adapt to any accidental inclinations of the instrument during insertion, since the roller adapts automatically, pulling the needle inwards.

From what has been described above it can thus be seen that the apparatus according to the present invention achieves the intended aim and objects, and in particular the fact is stressed that the automation of the needle insertion step, directly by means of an actuation system which is activated by the insertion of the needle, allows to eliminate operator contact with the instrument to be destroyed after the insertion step.

The needles are furthermore completely destroyed, and a very short stump with a sealed end is extracted.

The invention thus conceived is susceptible to numerous modifications and variations, all of which are within the scope of the inventive concept.

All the details may furthermore be replaced with other technically equivalent elements; thus for example, the cutting unit may be constituted by a laser beam unit with emitting blocks located at opposite sides of the article to be cut.

In practice, the materials employed, as well as the contingent shapes and dimensions, may be any according to the requirements.

Where technical features mentioned in any claim are followed by reference signs, those reference signs have been included for the sole purpose of increasing the intelligibility of the claims and accordingly, such reference signs do not have any limiting effect on the scope of each element identified by way of example by such reference signs.

I claim:

1. Apparatus for destroying surgical instruments comprising a containment body which includes an insertion plate for the reception of the surgical instruments to be destroyed and a panel made of an electrically conducting material, said plate and said panel being respectively electrically connected to a first pole and to a second pole of an electric current generator, characterized in that said plate is arranged on a traction and removal unit adapted to receive said instruments, to remove said instruments from a holding means, and to push said instruments against said panel so as to provoke a melting current discharge through the instruments, and in that an insertion sensor is further provided for activating said traction and removal unit as soon as the instruments are inserted in said insertion plate.

2. Apparatus according to claim 1, characterized in that said insertion plate is provided with a hole for the insertion of needles and with a slot for the insertion of scalpels and blades.

3. Apparatus according to claim 1, characterized in that said unit for the removal and traction of the instruments to be destroyed comprises first and second rollers which rotate in mutually opposite directions and are supported by first and second frames which are mutually pivoted at a motion transmission shaft, elastic means being furthermore provided which act between said frames and a fixed structure of a framework of the apparatus in order to create an elastic contrast for the coupling of said rollers by contact.

4. Apparatus according to claim 3, further comprising motor means equipped with a reduction unit and connected to a bevel gear which meshes with bevel pinions respectively keyed on half-shafts which constitute said motion transmission shaft and which extend in a rotation axis of said frames, a toothed gear being connected to each one of said half-shafts, a toothed belt winding around said gear and meshing with a toothed pinion keyed on the shaft of the related roller.

5. Apparatus according to claim 3, characterized in that said apparatus further includes a cutting unit provided with a cutting frame oscillatably mounted and actuated by eccentric elements moved by actuation shafts of the supporting frames of said rollers.

6. Apparatus according to claim 1, characterized in that said insertion sensor comprises a toggle contact drivable upon a surgical instrument to be destroyed making a connection between said insertion plate and traction rollers of said unit, which are connected to different poles of an electric generator.

7. Apparatus according to claim 6, characterized in that said apparatus further includes a sliding contact for the electrical connection of said rollers.

8. Apparatus according to claim 1, characterized in that said insertion sensor comprises an optical emitter for emitting a light beam which is arranged at the instrument insertion region and a receiving photocell which drives the contact for actuating said motor.

9. Apparatus according to claim 1, characterized in that a frame of the apparatus supports a striker block arranged at an anvil located inside said containment body substantially at said insertion plate below said insertion holes of said insertion plate, said striker block being electrically connected to the same electrical connection pole as said panel in order to cut said instruments by melting and compression.

* * * * *